(12) United States Patent
Wei et al.

(10) Patent No.: US 10,988,777 B2
(45) Date of Patent: Apr. 27, 2021

(54) METHOD FOR INDUCING CCR5Δ32 DELETION BY USING CRISPR-CAS9 GENOME EDITING TECHNIQUE

(71) Applicant: NANKAI UNIVERSITY, Tianjin (CN)

(72) Inventors: Min Wei, Tianjin (CN); Chunxia Qi, Tianjin (CN)

(73) Assignee: Nankai University, Tianjin (CN)

( * ) Notice: Subject to any disclaimer, the term of this patent is extended or adjusted under 35 U.S.C. 154(b) by 0 days.

(21) Appl. No.: 15/518,252

(22) PCT Filed: Apr. 12, 2016

(86) PCT No.: PCT/CN2016/079007
§ 371 (c)(1),
(2) Date: Apr. 11, 2017

(87) PCT Pub. No.: WO2017/124652
PCT Pub. Date: Jul. 27, 2017

(65) Prior Publication Data
US 2018/0363001 A1    Dec. 20, 2018

(30) Foreign Application Priority Data
Jan. 18, 2016    (CN) .......................... 201610028603.1

(51) Int. Cl.
| | |
|---|---|
| *C12N 15/86* | (2006.01) |
| *C12N 9/22* | (2006.01) |
| *C12N 15/11* | (2006.01) |
| *C12N 15/10* | (2006.01) |
| *C12N 15/113* | (2010.01) |
| *C12N 15/90* | (2006.01) |
| *A61K 48/00* | (2006.01) |

(52) U.S. Cl.
CPC ............... *C12N 15/86* (2013.01); *C12N 9/22* (2013.01); *C12N 15/102* (2013.01); *C12N 15/11* (2013.01); *C12N 15/1138* (2013.01); *C12N 15/907* (2013.01); *A61K 48/00* (2013.01); *C12N 2310/20* (2017.05); *C12N 2320/34* (2013.01); *C12N 2740/15045* (2013.01); *C12N 2740/16043* (2013.01)

(58) Field of Classification Search
CPC .... C12N 15/11; C12N 15/86; C12N 15/1138; C12N 15/102; C12N 15/907; C12N 9/22
See application file for complete search history.

(56) References Cited

U.S. PATENT DOCUMENTS

2015/0071889 A1* 3/2015 Musunuru ............ C12N 15/907
424/93.7

OTHER PUBLICATIONS

Cribbs et al.; Simplified production and concentration of lentiviral vectors to achieve high transduction in primary human T cells; BMC Biotechnology, vol. 13, No. 98, pp. 1-8, published Nov. 12, 2013 (Year: 2013).*

* cited by examiner

*Primary Examiner* — Antonio Galisteo Gonzalez
(74) *Attorney, Agent, or Firm* — Limin Wen

(57) ABSTRACT

The present invention relates to a new method for successfully inducing the mutation of cell chemokine receptor CCR5 gene into CCR5Δ32 deletion gene by using the CRISPR-Cas9 genome editing technique. CCR5 is an important co-receptor for entry of Human Immunodeficiency Virus (HIV) into human host cells. CCR5Δ32 deletion is a 32-bp deletion in CCR5 coding region, which results in change and premature termination in the sequence following the $185^{th}$ amino acid. Biallelic homozygous deletion of CCR5Δ32 is naturally resistant to HIV infection, i.e., the people carrying this mutation can't be infected by HIV. The present invention uses both lentiviral packaging system and the CRISPR technique to induce CCR5Δ32 deletion. Due to the characteristics of a wide range of *Lentivirus* infection, the invention can be applied to cells such as bone marrow stem cells and CD4+ T cells and can be expected to be the therapeutic drug for HIV/AIDS infection or other diseases.

4 Claims, 6 Drawing Sheets
Specification includes a Sequence Listing.

CCR5 protein

CCR5 gene

TTTCCATACAGTCAGTATCAATTCTGGAAGAATTTCCAGACATTAAAGATA CCR5 WT
TTTCCATACA —————————————————————————————————-TTAAAGATA CCR5 Δ32
TTTCCATACA —————————————————————————————————-TTAAAGATA monoclone 1
TTTCCATACA —————————————————————————————————-TTAAAGATA monoclone 2

METHOD FOR INDUCING CCR5Δ32 DELETION BY USING CRISPR-CAS9 GENOME EDITING TECHNIQUE

REFERENCE TO RELATED APPLICATION

This application claims the benefits of the filing dates of Chinese patent application Serial No. 201610028603.1 filed on Jan. 18, 2016 and PCT Patent Application Serial No. PCT/CN2016/079007 filed on Apr. 12, 2016, entitled "Method for Inducing CCR5Δ32 Deletion by Using CRISPR-Cas9 Genome Editing Technique". The teachings of the entire referenced applications are incorporated herein by reference.

SEQUENCE LISTING

The instant application contains an Amended Sequence Listing which has been submitted electronically in ASCII format and is hereby incorporated by reference in its entirety. Said ASCII copy, created on Feb. 8, 2021, is named "updatedsequencelisting02082021.txt" and is 10 KB bytes in size.

FIELD OF THE INVENTION

The present invention belongs to the biomedical field, and relates to a novel method for inducing CCR5Δ32 deletion by using a CRISPR-Cas9 genome editing technique.

BACKGROUND

Acquired Immune Deficiency Syndrome (AIDS) caused by Human Immunodeficiency Virus (HIV) (also named AIDS virus) has been widespread for over 30 years all over the world. HIV/AIDS is a kind of highly infectious disease. HIV can directly attack the human immune system, thus resulting in human immune functional deficiency. Ultimately, the patients will die due to a variety of opportunistic infections and/or tumors. HIV is mainly classified into two types, HIV-1 and HIV-2. HIV-1 causes the pandemic all over the world. HIV-2 is only limited in some parts of Africa and in scattered reports of other areas. According to the report of the World Health Organization (WHO), by the end of 2013, there were about 65 million people affected with HIV-1 in total in the world. Among them, about 35 million people were living with HIV, and about 30 million people already died. In 2013, the new cases infected with HIV-1 were about 2.1 million, and the patients who died of AIDS were about 1.5 million in the same year (http://www.who.int). Up to now, there is still no effective anti-HIV vaccine. Although much progress is made in the anti-retroviral drugs and the anti-retroviral therapy (ART) and the virus replication can be effectively controlled, HIV in patient's body can't be thoroughly eradicated. Therefore, HIV/AIDS can't be fundamentally cured. Also, the anti-retroviral therapy requires a long period of time, which will bring side effects, huge mental stress and economic stress in patients.

China was also suffered from HIV/AIDS. In 1989, one case was reported who was a hemophilia patient infected by HIV during blood transfusion. In 1990s', an outbreak of HIV infection happened among the drug-users in YunNan province. Entering the 21th century, the HIV transmission gradually transfers from blood collection and drug-use to sexual transmission (including homosexual and heterosexual transmissions) in our country. According to the report of the Ministry of Health of China and the Joint United Nations Program on HIV/AIDS, by the end of 2011, it is estimated that there were approximately 780,000 (620,000~940,000) people living with HIV in China. Among them, the ratio of female was 28.6%; AIDS patients were 154,000 people (146,000~162,000 people); the HIV morbility of whole population was 0.058% (0.046%~0.070%). It was estimated that the new HIV-1 infected people was approximately 48,000 people (41,000~54,000 people) in 2011 and the number of AIDS-related death was approximately 28,000 people (25,000~31,000 people) in 2011. As well, the HIV epidemic situation is not optimistic in China.

HIV mainly attacks human immune system by firstly identifying and binding CD4+ receptor on cell surface (CD, the abbreviation of Cluster of Differentiation, is the generic term of a class of differentiation antigens located on the surface of cell membrane. The serial number following the "CD" represents one or a class of differentiation antigen molecules). CD4+ receptor is essential for HIV infection. In the following process, HIV molecule needs to interact with co-receptors. The main co-receptors are chemokine receptor CCR5 (C-C Chemokine receptor type 5) and chemokine receptor CXCR4 (C-X-C chemokine receptor type 4). After HIV successfully binds the receptor and the co-receptor, the changes occur in viral structure and cell membrane, which causes virus-cell fusion and virus entry into the target cells. CCR5 is a seven-transmembrane protein (As shown in FIG. 1) and contains 352 amino acids. CCR5 is a kind of normal chemokine receptor on the cell surface, and is also a major co-receptor by which HIV enters into the target CD4+ cells. It was found that some of the European Caucasians enabled to resist HIV infection. The sequencing analysis indicates that normal CCR5 gene of these people is mutated into CCR5Δ32 gene. In CCR5Δ32 deletion, a 32-bp from position 794 to position 825 in CCR5 gene coding region is deleted (As shown in FIG. 2), which makes the changes on amino acids behind position 185 and results in premature termination in protein translation and generation of deleted protein only with 215 amino acids. This kind of deleted protein can't be generally positioned on cell membrane, but can only stay in endoplasmic reticulum because of the loss of three transmembrane regions 5, 6, and 7. The cell having this mutation is provided with the capability to resist HIV infection as it lacks the co-receptors required to fuse with the virus. If both of the CCR5 alleles inside a cell carry Δ32 deletion, the cell is a homozygote and recorded as CCR5Δ32/Δ32; if only one is Δ32 deletion and the other is the wild type, the cell is a heterozygote and recorded as CCR5Δ32/WT. The study indicates that CCR5Δ32/Δ32 homozygous deletion is naturally resistant to HIV infection, i.e., the patients can't be infected by HIV. The people with CCR5Δ32/WT heterozygous deletion are able to extend onset period of AIDS.

In 2009, German doctors reported that a HIV-infected person named Timothy Brown in Berlin was diagnosed with acute myeloid leukemia after he was diagnosed with HIV infection for 10 years and received four-year anti-retroviral therapy (ART). The doctors gave him allogeneic stem cell transplantation and the donor of stem cell transplantation is CCR5Δ32/Δ32 homozygote. Virus rebound was not found after the second stem cell transplantation and stop of ART for 20 months. The more important was that the virus rebound was still not found after he stopped ART for 7 years. This is the first case in the world that HIV-infected person is considered to be cured or functionally cured, i.e., there is no virus rebound after the stop of ART.

It is investigated that CCR5Δ32/Δ32 deletion homozygote rate is slightly higher in the European Caucasian population (4-10%), but few exists in Africa and Asian population, only 0-0.19% among Chinese. In China, it is unrealistic to reproduce "the Berlin Patient" case by attempting to find CCR5Δ32/Δ32 deletion donors to perform bone marrow transplantation because of the exiguous donors and the risk of allograft rejection. The present invention attempts to use a new method to carry out this mission.

HIV genome is ribonucleic acid (RNA). The classification of HIV belongs to the genus *Lentivirus* of the Retroviridae family, because HIV has reverse transcriptase. Virus of this genus is known as *Lentivirus* because it needs the long latent period and the slow disease onset course to cause disease. Lentiviral vector is a gene therapy vector, which is developed based on HIV-1. In lentiviral vector, HIV-1 pathogenic gene is removed and the process of virus infection of a cell is simulated. The lentiviral vector has the ability to infect both dividing and non-dividing cells and is applied for the cells, which are harder to be transfected with an exogenous gene, such as lymphocytes, primary cells, neuronal cells, stem cells, and etc. This vector can effectively integrate the exogenous gene into host cell genome in order to express the exogenous gene stably for a long period of time. During the experiment, it is necessary to co-transfect the target plasmid carrying the exogenous gene and packaging plasmid into packaging cells in order to produce lentiviral particles. The well-packaged pseudovirions will be secreted into an extracellular medium. After centrifugation, supernatant is directly used for infection of host cells. Thus, the well-packaged lentiviral particles infect the host cells, the target plasmid is reversely transcribed to cDNA by reverse transcriptase and integrated into the host cell genome by integrase so as to stably express the exogenous interest gene in the host cells for a long period of time.

Recently, a new genome editing technique—clustered regularly interspaced short palindromic repeat (CRISPR) and CRISPR associated protein (Cas) technique has been paid attention gradually and widely used. CRISPR sequence generally exists in bacteria and archaebacteria. It is a kind of immune defense system formed in evolving process, in which bacteria fights against attack of virus of the bacteria—phage. CRISPR locus is generally composed of short highly conserved repeats. Spacers with different length separate the repeats. The spacers are derived from phage or exogenous DNA sequence, which is similar to immunologic memory acquisition. When the phages or exogenous DNA with the same sequence infects bacteria again, the bacteria can recognize and bind the exogenous sequence with Cas proteins, and then the exogenous sequence is cleaved under the action of a series of Cas related proteins in order to achieve the purpose of protecting itself. CRISPR system can be classified into three types according to different Cas proteins involving in defense process. Among them, type II CRISPR system is widely used because of its simplicity. It only requires a Cas9 protein to complete entire cutting process of the exogenous gene sequence. Under natural condition, the type II CRISPR system also requires crRNA (CRISPR RNA) and transcrRNA (trans-activating crRNA) to together guide Cas9 to recognize and cleave the exogenous sequence. For simplicity of this system, the commonly used is crRNA and transcrRNA complex-guide RNA (gRNA), which helps the Cas9 protein to recognize the target sequence. In CRISPR-Cas9 technique, gRNA recognizes the protospacer adjacent motif (PAM) and binds the target sequence. Thus, under the guide of gRNA, the double-stranded DNA at target site is cleaved by the nuclease Cas9, which leads to double-strand break and induction of cell self-repair process. The cell can be repaired by two ways-homologous recombination or non-homologous end joining. These two kinds of repair ways can result in specific gene modification or deletion or insertion of a small number of nucleotide residues, and thus resulting in mutation of the target sequences.

There have been some reports that this technique is used to abrogate the entire CCR5 gene. However, if the entire CCR5 gene is destroyed, the potential risk is unknown. The CCR5Δ32 deletion has been already present in the population. The people with this mutation can survive healthily without any abnormality. Therefore, it is more significant to induce CCR5Δ32 deletion.

The present invention successfully expresses CRISPR-Cas9 in lymphocytes and successfully obtains the monoclonal cells with CCR5Δ32/Δ32 homozygous genotype by using the lentiviral packaging system. It provides a new way for people to treat HIV/AIDS at the genetic level.

SUMMARY OF THE INVENTION

Technical Problem

An object of the present invention is to solve the problem of the artificial induction of CCR5Δ32 deletion, and to provide a method for inducing CCR5Δ32/Δ32 deletion of HIV co-receptor by using CRISPR-Cas9 genome editing technique, in order to provide a new therapeutic drug to cure HIV/AIDS.

Technical Solution

The present invention provides a method for inducing CCR5Δ32 deletion by using the CRISPR-Cas9 genome editing technique. This method successfully induces the CCR5Δ32 deletion by using CRISPR-Cas9 genome editing technique. Specifically, this method includes:

First, design of a guide RNA (gRNA)

For the purpose of obtaining CCR5Δ32/Δ32 homozygous cells, a pair of gRNAs is designed for target sequences on both sides of CCR5Δ32. The left side target DNA sequences corresponding to gRNA are listed as SEQ ID No.1 and SEQ ID Nos. 3-19; the right side target DNA sequences corresponding to the gRNA are also listed as SEQ ID No.2 and SEQ ID Nos. 20-36. We found that the result of Cas9 nuclease cleavage after selecting these two target sequences was completely the same as natural CCR5Δ32 deletion (As shown in FIG. 2, Cas9 cleavage sites are marked with arrowheads).

A pair of gRNAs is selected from any sequence of the left side target DNA sequences (SEQ ID No.1 and SEQ ID Nos. 3-19) and any sequence of the right side target DNA sequences (SEQ ID No.2 and SEQ ID Nos. 20-36), for example, a pair of gRNAs can be selected as a combination of SEQ ID No.1 and any sequence from SEQ ID Nos. 20-36 or SEQ ID No.2; a pair of gRNAs can be selected as a combination of SEQ ID No.3 and any sequence from SEQ ID Nos. 20-36 or SEQ ID No.2; and so on, a pair of gRNAs can be selected as a combination of SEQ ID No.19 and any sequence from SEQ ID Nos. 20-36 or SEQ ID No.2; a pair of gRNAs can be selected as a combination of SEQ ID No.2 and any sequence from SEQ ID Nos. 3-19 or SEQ ID No.1; a pair of gRNAs can be selected as a combination of SEQ ID No.20 and any sequence from SEQ ID Nos. 3-19 or SEQ ID No.1; and so on, a pair of gRNAs can be selected as a combination of SEQ ID No.36 and any sequence from SEQ ID Nos. 3-19 or SEQ ID No.1.

Due to the fault tolerance of CRISPR-Cas9, it can also be identified even if some individual base is changed. Thus, it will be within the protection scope of the present invention as long as the DNA sequences corresponding to gRNA with the seed DNA sequences "5' gactgta 3'" and "5' taatgtc 3'" is for the CCR5Δ32 deletion.

Second, according to the gRNA designed in the first step, the DNA sequences corresponding to gRNAs are inserted into the CRISPR-Cas9 plasmid vector for constructing functional plasmid. The plasmid has the following characteristics:

① The plasmid carries the Cas9 nuclease expression reading frame, other associated gene sequences of the CRISPR and lentiviral packaging signals. The plasmid map is shown in FIG. 3 (the plasmid vector lenti-CRISPR-v2 is from Dr. Feng Zhang Laboratory at the Massachusetts Institute of Technology.).

② The plasmid is designed for the production of gRNAs targeting both sides of CCR5Δ32 locus, as described in the first step; The study indicated that a cleavage for the target sequence at the same place can not only be done by using the wild-type Cas9 nuclease; but also be done by using two Cas9 nickases (Cas9 mutant). Thus, the object of the present invention can also be achieved by using the Cas9 nickase or the Cas9 mutants, or by using another nuclease such as Fok I.

Third, preparation of a lentiviral particle encapsulated with CRISPR-Cas9 plasmid:

The CRISPR-Cas9 plasmid constructed in the second step is transfected into the HEK293T cells together with the packaging plasmids PMD2.G and psPAX2.

After a period of time, cell supernatant is collected. The supernatant contains the lentiviral particle that we need.

Fourth, target cells are infected with the lentiviral particle obtained in the third step so that the CCR5Δ32/Δ32 homozygous deletion cells can be obtained.

Advantageous Effects (1) CCR5Δ32 deletion can be successfully induced by using a new CRISPR-Cas9 genome editing technique and the lentiviral packaging system.
(2) The successfully induced CCR5Δ32/Δ32 homozygous deletion cells can be used as a new drug for the treatment of HIV/AIDS.

In summary, the present invention successfully obtains CCR5Δ32/Δ32 homozygous deletion lymphocytes by using the lentiviral packaging system and the CRISPR-Cas9 technique at the same time. In addition, the invention can also be applied to various types of cells such as neuronal cells, hepatocytes, cardiomyocytes, tumor cells, endothelial cells, stem cells and lymphocytes due to a wide range of *Lentivirus* infection.

BRIEF DESCRIPTION OF THE DRAWINGS

FIG. 5 is representative microscope pictures illustrating the result of human Lymphocytic cell line Jurkat infected with *Lentivirus* vector carrying green fluorescence protein (GFP)

DETAILED DESCRIPTION

Examples

Example 1: Reconstruction of Plasmid Carrying CRISPR-Cas9 System and Preparation of Lentiviral Particles Encapsulated with the Reconstructed Plasmid 1. Selection and Design of gRNA (1) According to the object of experiment, a pair of gRNAs should be designed to edit CCR5 gene at the same time. However, due to the restriction of the CCR5 gene and the restriction of the PAM locus, the selection of the gRNA is limited. For the purpose of obtaining CCR5Δ32/Δ32 homozygous cells, a pair of gRNAs is designed for target sequences on both sides of CCR5Δ32. The left side target DNA sequences corresponding to gRNA are listed as SEQ ID No.1 and SEQ ID Nos. 3-19; the right side target DNA sequences corresponding to the gRNA are also listed as SEQ ID No.2 and SEQ ID Nos. 20-36. A pair of gRNAs is selected from any sequence of the left side target DNA sequences (SEQ ID No.1 and SEQ ID Nos. 3-19) and any sequence of the right side target DNA sequences (SEQ ID No.2 and SEQ ID Nos. 20-36), for example, a pair of gRNAs can be selected as a combination of SEQ ID No.1 and any sequence from SEQ ID Nos. 20-36 or SEQ ID No.2; a pair of gRNAs can be selected as a combination of SEQ ID No.3 and any sequence from SEQ ID Nos. 20-36 or SEQ ID No.2; and so on, a pair of gRNAs can be selected as a combination of SEQ ID No.19 and any sequence from SEQ ID Nos. 20-36 or SEQ ID No.2; a pair of gRNAs can be selected as a combination of SEQ ID No.2 and any sequence from SEQ ID Nos. 3-19 or SEQ ID No.1; a pair of gRNAs can be selected as a combination of SEQ ID No.20 and any sequence from SEQ ID Nos. 3-19 or SEQ ID No.1; and so on, a pair of gRNAs can be selected as a combination of SEQ ID No.36 and any sequence from SEQ ID Nos. 3-19 or SEQ ID No.1.

Figure 1:
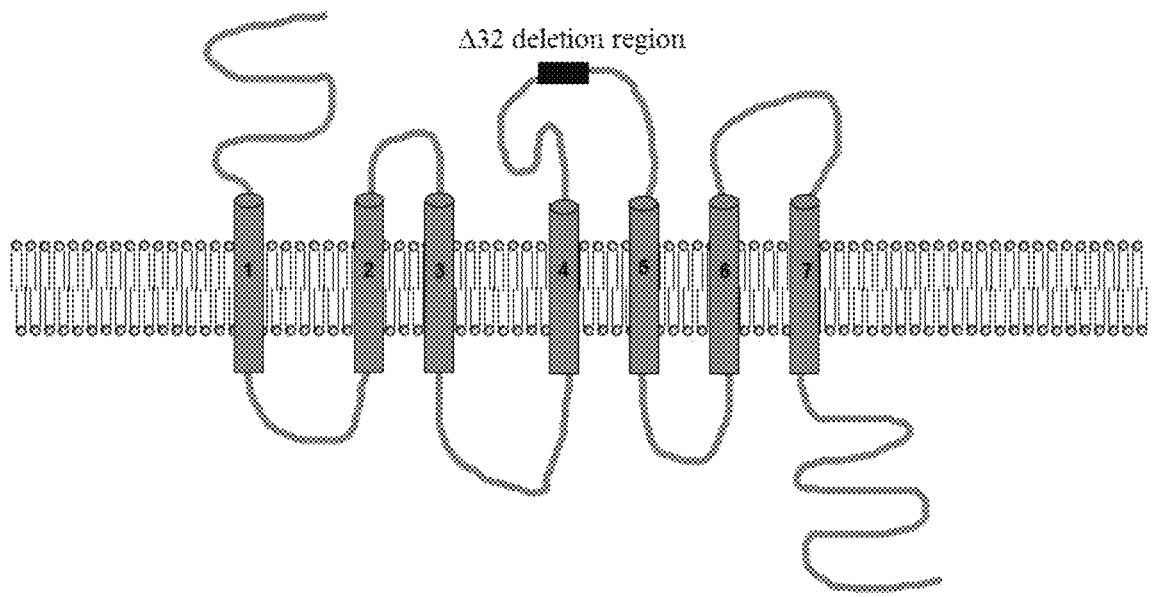
FIG. 1 is a diagram illustrating the CCR5 protein marked with 7 transmembrane regions.
Figure 2:
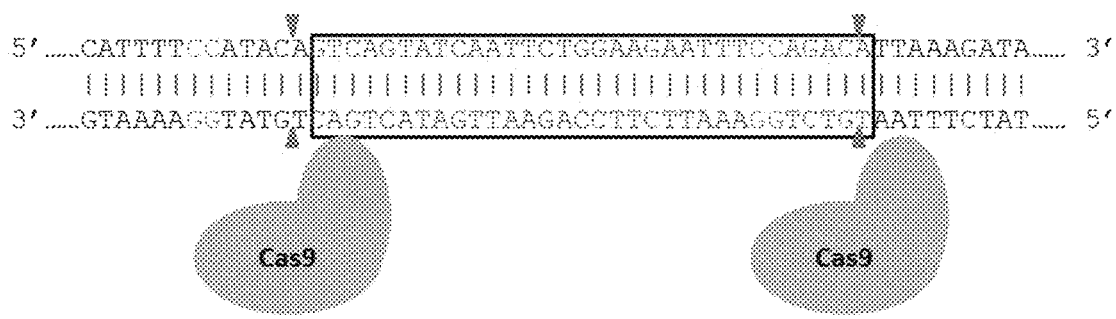
FIG. 2 is a diagram illustrating CCR5 gene. The block is CCR5Δ32 deletion gene (SEQ ID No. 39) and the arrowheads are Cas9 cleavage sites.
Figure 3:
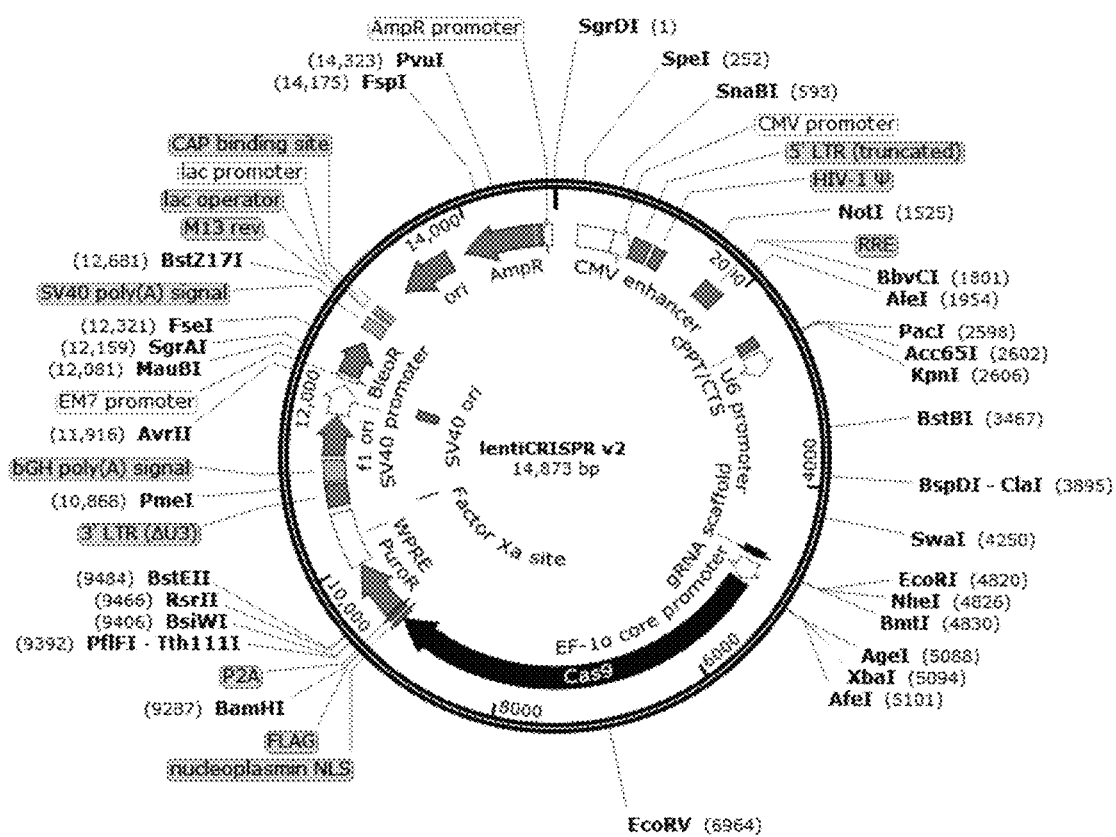
FIG. 3 is the lenti-CRISPR-v2 vector map used in experiment. The marked sites are restriction sites.
Figure 4:
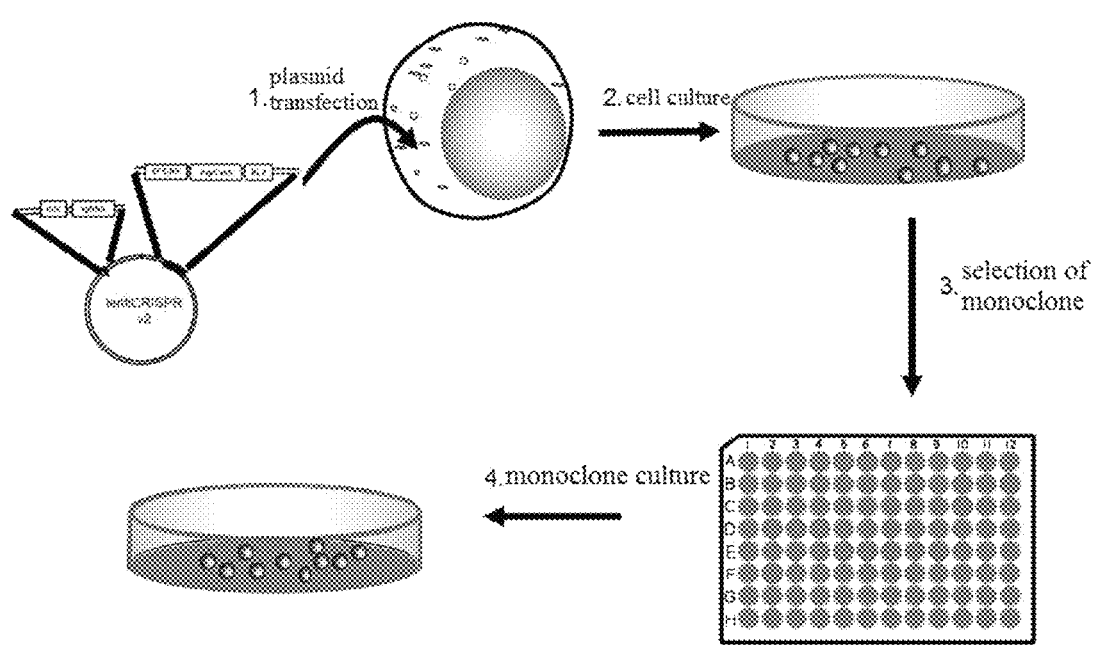
FIG. 4 is a flow chart of the entire process of the experiment.

(2) The reconstructed plasmid was obtained by adding a restriction enzyme cleavage site according to gRNA sequences, synthesizing DNAs, and ligating DNAs into BsmBI-digested lenti-CRISPR-v2 vector. The right insertion of the sequence was verified by sequencing. FIG. 4 shows the whole experimental process.

2. Preparation of Lentiviral Particles and Identification of Infection Efficiency Thereof (1) HEK293T cells were plated in 10 mm diameter dishes. Total cell number is 6×10$^6$. The next day, two kinds of lenti-CRISPR-v2 plasmids with a pair of corresponding gRNAs obtained from the first step and lentiviral packaging plasmids PMD2.G and psPAX2 were co-transfected into cells in the microgram ratio 1 µg:1 µg:1 µg:1 µg and the cells were incubated in thermostatic incubator containing 5% $CO_2$ at 37° C. for 16 h. Then, the resulting culture was centrifuged to remove the whole medium. The fresh DMEM complete medium (in which 10% fetal calf serum and two kinds of antibiotics Penicillin-Streptomycin were added) was added thereto for incubation. After 24 h, the cell supernatant was collected by centrifugation. This supernatant contains the lentiviral particles we needed. Aliquot the supernatant into 1.5 ml centrifuge tubes by 1 ml per tube and store in a refrigerator at −80° C. for use. Meanwhile, the pwpxld plasmid that can express the GFP protein was packaged into the lentiviral particle, so as to observe the efficiency of infection of lymphocytes by lentiviral particles.

Figure 5A:
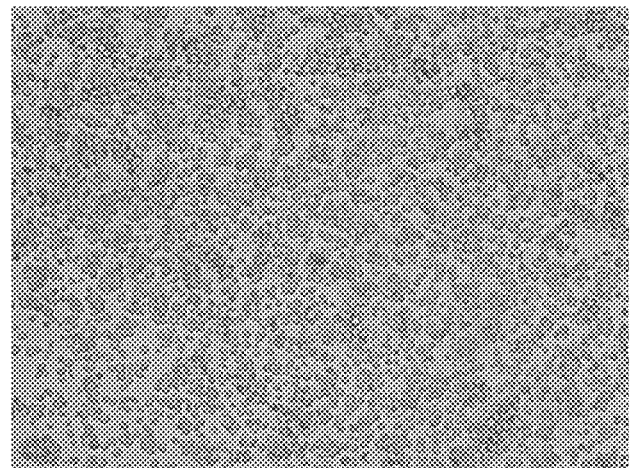
FIG. 5A is the picture under light microscope (magnification of 10×10)
Figure 5B:
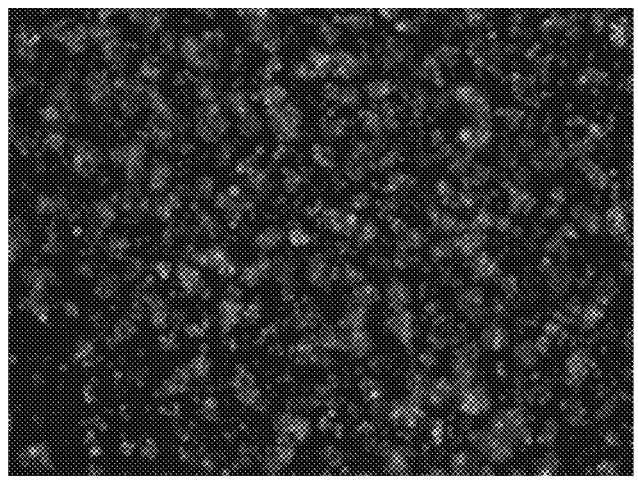
FIG. 5B is the picture under fluorescence microscope (the same vision, magnification of 10×10), the light white is the GFP positive cells, and the black is the GFP negative cells.

(2) Lymphocytes were plated in 6-well plates before infection. Total cell number per well was $2\times10^5$. The medium was the complete medium, which does not contain any antibiotics. The next day, the lentiviral particles encapsulated with pwpxld were added into cells. Polybrene that enables to increase the efficiency of virus infection was added at the same time and was adjusted to a concentration of 8 µg/ml. The resulting culture was centrifuged at 1600 rpm at 37° C. for 1 h. After centrifugation, the medium containing virus fluid was removed and a new complete medium was added. The expression of GFP in cells was observed after incubation for 48 h. The efficiency of *Lentivirus* infection can reach more than 80% depending on GFP expression situation in cells (see FIG. 5, the microscope photographs).

Example 2: The Result of Infecting Lymphocyte by the Lentiviral Particle Encapsulated with Reconstructed Plasmid Lenti-CRISPR-v2

1. Lymphocytes were plated in 6-well plates before infection. Total cell number per well was $2\times10^5$. The medium was the complete medium, which does not contain any antibiotics. The next day, the lentiviral particles encapsulated with lenti-CRISPR-v2 plasmid having corresponding gRNAs obtained in Example 1 and the lentiviral particle encapsulated with gRNA-free lenti-CRISPR-v2 plasmid were added into cell medium separately. Polybrene that enables to increase the efficiency of virus infection was added at the same time and was adjusted to a concentration of 8 µg/ml. The resulting culture was centrifuged at 1600 rpm at 37° C. for 1 h. After centrifugation, the medium containing virus fluid was removed and a new complete medium was added. The cells were collected by centrifugation after incubation for 72 h. Half of the collected cells were transferred to a new culture flask for continuous incubation. The other half was used to extract total genomic DNA from the cells for subsequent analysis.

Figure 6:
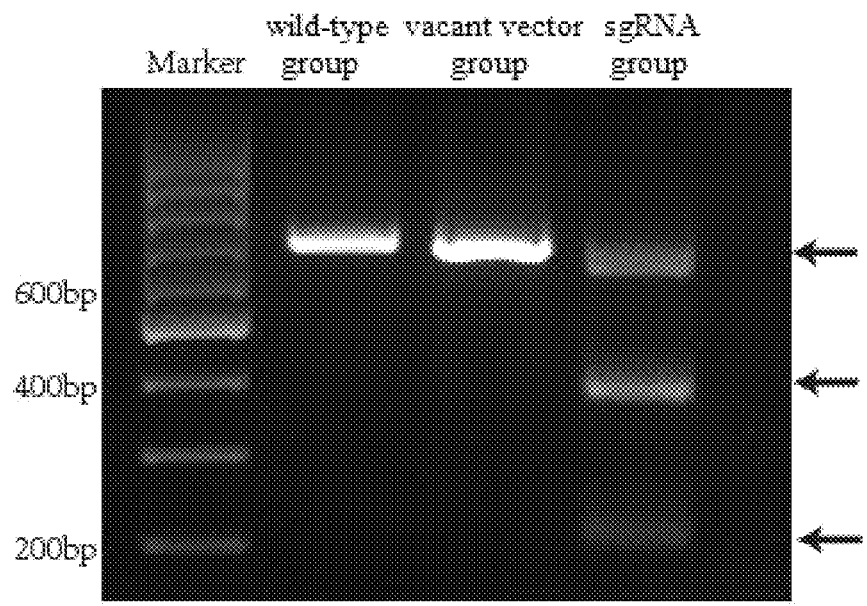
FIG. 6 is an agarose gel electrophoresis picture illustrating the efficiency of CRISPR-Cas9 system in CCR5 gene editing of lymphocyte cell line Jurkat detected by using T7 endonuclease (T7E1) digestion method.

2. Using the extracted genomic DNA of cells as a template, the sequence containing CCR5Δ32 locus was PCR-amplified with the forward primer SEQ ID No. 37 and the reverse primer SEQ ID No. 38. The editing efficiency of the CRISPR system was verified by T7 endonuclease (T7E1) digestion method (T7 endonuclease I, T7E1 in short, can identify and cut mismatched DNA). The experimental results were shown in FIG. 6. It can be seen from the figure that cleavage occurred in the group in which a pair of the lenti-CRISPR-v2 plasmids obtained in Example 1 was transfected, whereas cleavage did not occur in the gRNA-free empty vector group. It indicated our CRISPR-Cas9 system was working.

3. CRISPR-Cas9 system may result in the insertion or deletion of a different number of bases at the break since it would initiate the cell self-repair pathway after DNA double-strands of the target sequence was cleaved by the CRISPR-Cas9 system. In order to purify cell genotype and get monoclonal cells, 100 cells were first taken out and diluted to a volume of 1000 µl after counting. Then mixed thoroughly, 10 µl of the mixture was added to a 96-well plate separately. 200 µl of complete culture medium was added to each well. The resulting mixture was incubated in a 5% $CO_2$ incubator at 37° C. The next day, the cell number of each well was observed, and the wells with only one cell were selected and labeled for further culture. After two weeks, the monoclonal cells grown from a single cell were transferred to a 24-well plate for further culture. Until the plate was covered with cells, the cells were transferred to a 6-well plate for further culture.

Figure 7:
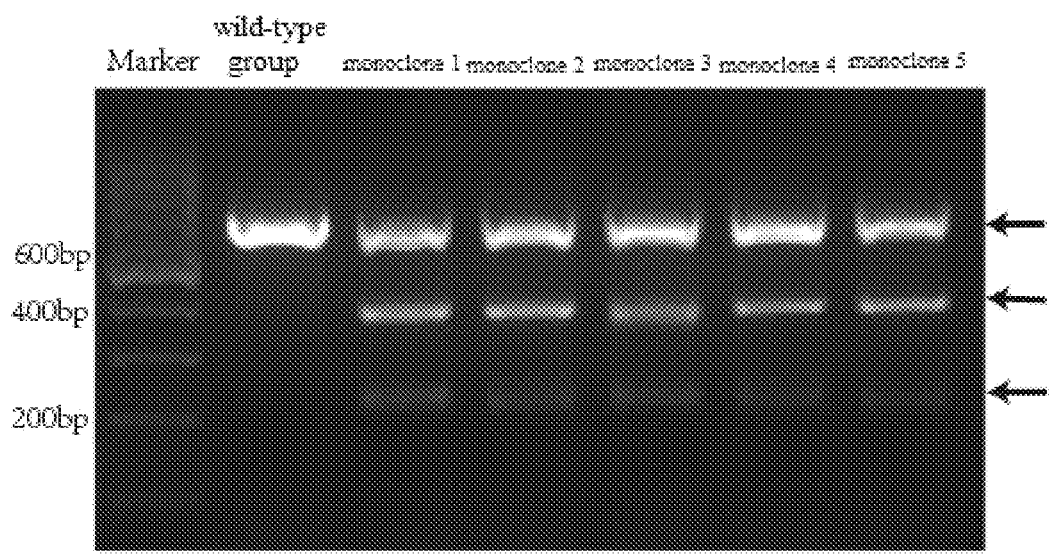
FIG. 7 is the CRISPR-Cas9 cleavage on CCR5 gene in different monoclonal cell groups detected by using T7E1 digestion method.

4. The monoclonal cells in the 6-well plate were collected as described above. Half of the cells was used for further culture and the other half was used for extracting cell genome. A CCR5 gene sequence was also amplified using the primers described above. Then the amplification products were preliminarily identified whether the CCR5 gene was mutated in these monoclonal cells by digesting with T7E1. The experimental results were shown in FIG. 7. It can be seen that cleavage occurred in the five monoclonal cell groups (FIG. 7), which indicated a CRISPR-Cas9-mediated mutation. In the next step, we would prove whether a CCR5Δ32 deletion may occur by sequencing.

Figures 8, 9:
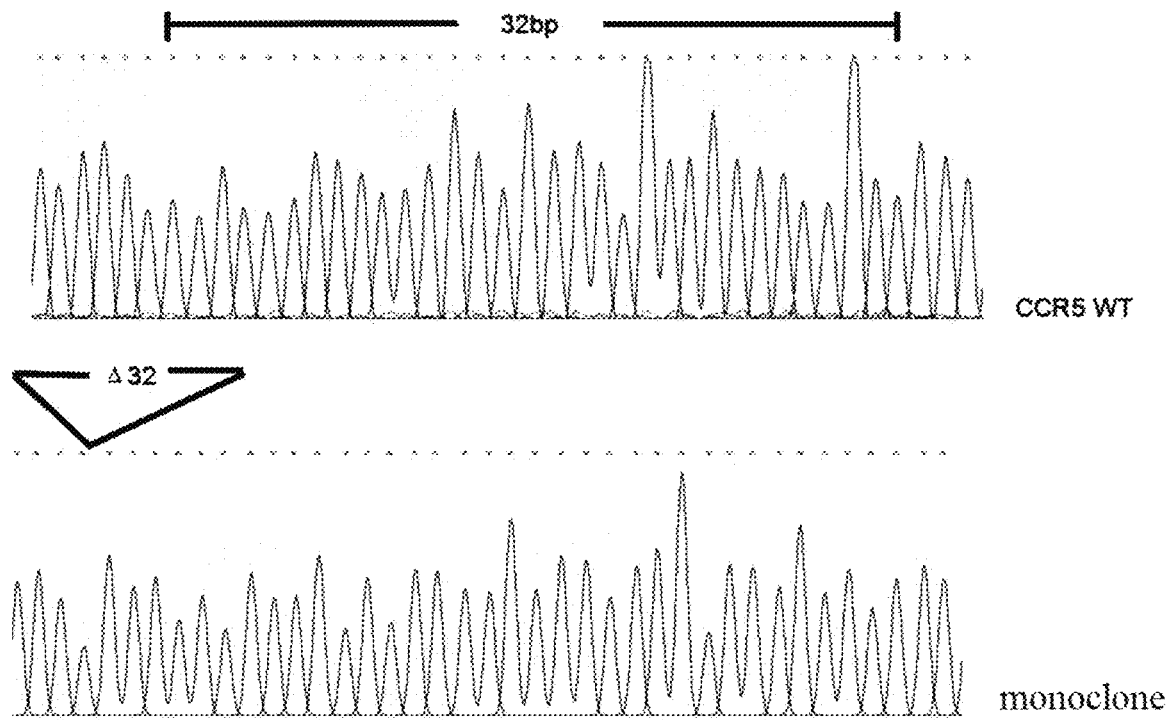
FIG. 8 shows the sequencing maps at CCR5Δ32 locus of wild-type cells and the obtained CCR5Δ32/Δ32 monoclonal cells.
FIG. 9 is a diagram illustrating sequence alignments of two obtained CCR5Δ32/Δ32 monoclonal cells (SEQ ID No. 41) and wild-type CCR5 cells (SEQ ID No. 42).

5. Five different monoclonal cells were selected for further analyzing. First, 1 µl of the PCR product of each monoclonal cell was taken out and ligated into the TA cloning vector in order to obtain 20 µl of ligation product, respectively. Then, 5 µl of the ligation product was taken out and transformed into *E. coli* competent cell DH5α. The single cloning was picked from plate and identified by sequencing. The result of sequencing indicated that among them, CCR5Δ32/Δ32 homozygous deletion happened in 3 monoclonal cells, and another two monoclonal cells had insertion or deletion of different numbers of bases happened at CCR5Δ32 locus. Partial sequencing chromatograms were shown in FIG. 8. Partial sequence alignments were shown in FIG. 9.

The present invention utilizes the lentiviral particle to encapsulate our designed CRISPR-Cas9 system to infect lymphocytes, and successfully induces CCR5Δ32/Δ32 homozygous deletion. Due to a wide range of *Lentivirus* infection, this system can also be used to infect various types of cells such as neuronal cells, hepatocytes, cardiomyocytes, tumor cells, endothelial cells, stem cells and lymphocytes.

What is claimed is:

1. A method for treating HIV/AIDS by inducing CCR5Δ32 deletion by using CRISPR-Cas9 genome editing technique, wherein the method comprises:
   i) designing a pair of guide RNAs (gRNA) for target sequences at both sides of CCR5Δ32, to obtain CCR5Δ32/Δ32 homozygous cells,
     wherein the DNA corresponding to the gRNA at the left side of CCR5Δ32 deletion sequence is selected from any one sequence of SEQ ID Nos. 3-19;
     wherein the DNA corresponding to the gRNA at the right side of CCR5Δ32 deletion sequence is selected from any one sequence of SEQ ID Nos. 20-36;
     wherein the DNA corresponding to the gRNA at the left side of CCR5Δ32 deletion sequence has the seed DNA sequence "5' gactgta 3'" and the DNA corresponding to the gRNA at the right side of CCR5Δ32 deletion sequence has the seed DNA sequence "5' taatgtc 3'";
   ii) constructing a functional plasmid by inserting the DNA sequences corresponding to the gRNAs designed in i) into a CRISPR-Cas9 plasmid vector,
     wherein the functional plasmid comprises:
       a. a Cas9 nuclease expression reading frame, other associated gene sequences of CRISPR, and lentiviral packaging signals; and b. the DNA sequences corresponding to the gRNAs at both sides of CCR5Δ32 locus, as described in i);

iii) preparing lentiviral particles encapsulating the functional plasmid by co-transfecting the functional plasmid constructed in ii) and the packaging plasmids PMD2.G and psPAX2 into HEK293T cells, and collecting cell supernatant after a period of time, wherein the supernatant contains the lentiviral particles; and iv) infecting target cells with the lentiviral particles obtained in iii) to obtain CCR5Δ32/Δ32 homozygous deletion cells which are used as a treatment for HIV/AIDS.

2. The method according to claim 1, wherein the Cas9 nuclease is Cas9 mutant selected from a Cas9 nickase or Cas9-Fok I fusion protein.

3. The method according to claim 1, wherein the CRISPR-Cas9 plasmid vector is a *Lentivirus* vector, an adenovirus vector, or any other plasmid vector with CRISPR-Cas9.

4. The method according to claim 1, wherein the co-transfecting in iii) is performed by using *Lentivirus* infection or plasmid direct transfection.

\* \* \* \* \*

SEQUENCE LISTING

<160> NUMBER OF SEQ ID NOS: 42

<210> SEQ ID NO 1

```
<211> LENGTH: 20
<212> TYPE: DNA
<213> ORGANISM: Artificial Sequence
<220> FEATURE:
<223> OTHER INFORMATION: synthesized

<400> SEQUENCE: 1
cagaattgat actgactgta                                                    20

<210> SEQ ID NO 2
<211> LENGTH: 20
<212> TYPE: DNA
<213> ORGANISM: Artificial Sequence
<220> FEATURE:
<223> OTHER INFORMATION: synthesized

<400> SEQUENCE: 2
agatgactat ctttaatgtc                                                    20

<210> SEQ ID NO 3
<211> LENGTH: 13
<212> TYPE: DNA
<213> ORGANISM: Artificial Sequence
<220> FEATURE:
<223> OTHER INFORMATION: synthesized

<400> SEQUENCE: 3
gatactgact gta                                                           13

<210> SEQ ID NO 4
<211> LENGTH: 14
<212> TYPE: DNA
<213> ORGANISM: Artificial Sequence
<220> FEATURE:
<223> OTHER INFORMATION: synthesized

<400> SEQUENCE: 4
tgatactgac tgta                                                          14

<210> SEQ ID NO 5
<211> LENGTH: 15
<212> TYPE: DNA
<213> ORGANISM: Artificial Sequence
<220> FEATURE:
<223> OTHER INFORMATION: synthesized

<400> SEQUENCE: 5
ttgatactga ctgta                                                         15

<210> SEQ ID NO 6
<211> LENGTH: 16
<212> TYPE: DNA
<213> ORGANISM: Artificial Sequence
<220> FEATURE:
<223> OTHER INFORMATION: synthesized

<400> SEQUENCE: 6
attgatactg actgta                                                        16

<210> SEQ ID NO 7
<211> LENGTH: 17
<212> TYPE: DNA
<213> ORGANISM: Artificial Sequence
<220> FEATURE:
<223> OTHER INFORMATION: synthesized

<400> SEQUENCE: 7
```
aattgatact gactgta                                                  17

<210> SEQ ID NO 8
<211> LENGTH: 18
<212> TYPE: DNA
<213> ORGANISM: Artificial Sequence
<220> FEATURE:
<223> OTHER INFORMATION: synthesized

<400> SEQUENCE: 8
gaattgatac tgactgta                                                 18

<210> SEQ ID NO 9
<211> LENGTH: 19
<212> TYPE: DNA
<213> ORGANISM: Artificial Sequence
<220> FEATURE:
<223> OTHER INFORMATION: synthesized

<400> SEQUENCE: 9
agaattgata ctgactgta                                                19

<210> SEQ ID NO 10
<211> LENGTH: 21
<212> TYPE: DNA
<213> ORGANISM: Artificial Sequence
<220> FEATURE:
<223> OTHER INFORMATION: synthesized

<400> SEQUENCE: 10
ccagaattga tactgactgt a                                             21

<210> SEQ ID NO 11
<211> LENGTH: 22
<212> TYPE: DNA
<213> ORGANISM: Artificial Sequence
<220> FEATURE:
<223> OTHER INFORMATION: synthesized

<400> SEQUENCE: 11
tccagaattg atactgactg ta                                            22

<210> SEQ ID NO 12
<211> LENGTH: 23
<212> TYPE: DNA
<213> ORGANISM: Artificial Sequence
<220> FEATURE:
<223> OTHER INFORMATION: synthesized

<400> SEQUENCE: 12
ttccagaatt gatactgact gta                                           23

<210> SEQ ID NO 13
<211> LENGTH: 24
<212> TYPE: DNA
<213> ORGANISM: Artificial Sequence
<220> FEATURE:
<223> OTHER INFORMATION: synthesized

<400> SEQUENCE: 13
cttccagaat tgatactgac tgta                                          24

<210> SEQ ID NO 14
<211> LENGTH: 25
<212> TYPE: DNA

<213> ORGANISM: Artificial Sequence
<220> FEATURE:
<223> OTHER INFORMATION: synthesized

<400> SEQUENCE: 14
tcttccagaa ttgatactga ctgta                                     25

<210> SEQ ID NO 15
<211> LENGTH: 26
<212> TYPE: DNA
<213> ORGANISM: Artificial Sequence
<220> FEATURE:
<223> OTHER INFORMATION: synthesized

<400> SEQUENCE: 15
ttcttccaga attgatactg actgta                                    26

<210> SEQ ID NO 16
<211> LENGTH: 27
<212> TYPE: DNA
<213> ORGANISM: Artificial Sequence
<220> FEATURE:
<223> OTHER INFORMATION: synthesized

<400> SEQUENCE: 16
attcttccag aattgatact gactgta                                   27

<210> SEQ ID NO 17
<211> LENGTH: 28
<212> TYPE: DNA
<213> ORGANISM: Artificial Sequence
<220> FEATURE:
<223> OTHER INFORMATION: synthesized

<400> SEQUENCE: 17
aattcttcca gaattgatac tgactgta                                  28

<210> SEQ ID NO 18
<211> LENGTH: 29
<212> TYPE: DNA
<213> ORGANISM: Artificial Sequence
<220> FEATURE:
<223> OTHER INFORMATION: synthesized

<400> SEQUENCE: 18
aaattcttcc agaattgata ctgactgta                                 29

<210> SEQ ID NO 19
<211> LENGTH: 30
<212> TYPE: DNA
<213> ORGANISM: Artificial Sequence
<220> FEATURE:
<223> OTHER INFORMATION: synthesized

<400> SEQUENCE: 19
gaaattcttc cagaattgat actgactgta                                30

<210> SEQ ID NO 20
<211> LENGTH: 13
<212> TYPE: DNA
<213> ORGANISM: Artificial Sequence
<220> FEATURE:
<223> OTHER INFORMATION: synthesized

<400> SEQUENCE: 20
tatctttaat gtc                                                  13

<210> SEQ ID NO 21
<211> LENGTH: 14
<212> TYPE: DNA
<213> ORGANISM: Artificial Sequence
<220> FEATURE:
<223> OTHER INFORMATION: synthesized

<400> SEQUENCE: 21
ctatctttaa tgtc          14

<210> SEQ ID NO 22
<211> LENGTH: 15
<212> TYPE: DNA
<213> ORGANISM: Artificial Sequence
<220> FEATURE:
<223> OTHER INFORMATION: synthesized

<400> SEQUENCE: 22
actatcttta atgtc          15

<210> SEQ ID NO 23
<211> LENGTH: 16
<212> TYPE: DNA
<213> ORGANISM: Artificial Sequence
<220> FEATURE:
<223> OTHER INFORMATION: synthesized

<400> SEQUENCE: 23
gactatcttt aatgtc          16

<210> SEQ ID NO 24
<211> LENGTH: 17
<212> TYPE: DNA
<213> ORGANISM: Artificial Sequence
<220> FEATURE:
<223> OTHER INFORMATION: synthesized

<400> SEQUENCE: 24
tgactatctt taatgtc          17

<210> SEQ ID NO 25
<211> LENGTH: 18
<212> TYPE: DNA
<213> ORGANISM: Artificial Sequence
<220> FEATURE:
<223> OTHER INFORMATION: synthesized

<400> SEQUENCE: 25
atgactatct ttaatgtc          18

<210> SEQ ID NO 26
<211> LENGTH: 19
<212> TYPE: DNA
<213> ORGANISM: Artificial Sequence
<220> FEATURE:
<223> OTHER INFORMATION: synthesized

<400> SEQUENCE: 26
gatgactatc tttaatgtc          19

<210> SEQ ID NO 27
<211> LENGTH: 21
<212> TYPE: DNA
<213> ORGANISM: Artificial Sequence
<220> FEATURE:

<223> OTHER INFORMATION: synthesized

<400> SEQUENCE: 27
aagatgacta tctttaatgt c                                               21

<210> SEQ ID NO 28
<211> LENGTH: 22
<212> TYPE: DNA
<213> ORGANISM: Artificial Sequence
<220> FEATURE:
<223> OTHER INFORMATION: synthesized

<400> SEQUENCE: 28
caagatgact atctttaatg tc                                              22

<210> SEQ ID NO 29
<211> LENGTH: 23
<212> TYPE: DNA
<213> ORGANISM: Artificial Sequence
<220> FEATURE:
<223> OTHER INFORMATION: synthesized

<400> SEQUENCE: 29
ccaagatgac tatctttaat gtc                                             23

<210> SEQ ID NO 30
<211> LENGTH: 24
<212> TYPE: DNA
<213> ORGANISM: Artificial Sequence
<220> FEATURE:
<223> OTHER INFORMATION: synthesized

<400> SEQUENCE: 30
cccaagatga ctatctttaa tgtc                                            24

<210> SEQ ID NO 31
<211> LENGTH: 25
<212> TYPE: DNA
<213> ORGANISM: Artificial Sequence
<220> FEATURE:
<223> OTHER INFORMATION: synthesized

<400> SEQUENCE: 31
ccccaagatg actatcttta atgtc                                           25

<210> SEQ ID NO 32
<211> LENGTH: 26
<212> TYPE: DNA
<213> ORGANISM: Artificial Sequence
<220> FEATURE:
<223> OTHER INFORMATION: synthesized

<400> SEQUENCE: 32
gccccaagat gactatcttt aatgtc                                          26

<210> SEQ ID NO 33
<211> LENGTH: 27
<212> TYPE: DNA
<213> ORGANISM: Artificial Sequence
<220> FEATURE:
<223> OTHER INFORMATION: synthesized

<400> SEQUENCE: 33
agccccaaga tgactatctt taatgtc                                         27

```
<210> SEQ ID NO 34
<211> LENGTH: 28
<212> TYPE: DNA
<213> ORGANISM: Artificial Sequence
<220> FEATURE:
<223> OTHER INFORMATION: synthesized

<400> SEQUENCE: 34
cagccccaag atgactatct ttaatgtc                                    28

<210> SEQ ID NO 35
<211> LENGTH: 29
<212> TYPE: DNA
<213> ORGANISM: Artificial Sequence
<220> FEATURE:
<223> OTHER INFORMATION: synthesized

<400> SEQUENCE: 35
ccagccccaa gatgactatc tttaatgtc                                   29

<210> SEQ ID NO 36
<211> LENGTH: 30
<212> TYPE: DNA
<213> ORGANISM: Artificial Sequence
<220> FEATURE:
<223> OTHER INFORMATION: synthesized

<400> SEQUENCE: 36
accagcccca agatgactat ctttaatgtc                                  30

<210> SEQ ID NO 37
<211> LENGTH: 20
<212> TYPE: DNA
<213> ORGANISM: Artificial Sequence
<220> FEATURE:
<223> OTHER INFORMATION: synthesized

<400> SEQUENCE: 37
tcttcttcat catcctcctg                                             20

<210> SEQ ID NO 38
<211> LENGTH: 18
<212> TYPE: DNA
<213> ORGANISM: Artificial Sequence
<220> FEATURE:
<223> OTHER INFORMATION: synthesized

<400> SEQUENCE: 38
gtttggcaat gtgctttt                                               18

<210> SEQ ID NO 39
<211> LENGTH: 54
<212> TYPE: DNA
<213> ORGANISM: Artificial Sequence
<220> FEATURE:
<223> OTHER INFORMATION: part of DNA of CCR5 gene

<400> SEQUENCE: 39
cattttccat acagtcagta tcaattctgg aagaatttcc agacattaaa gata       54

<210> SEQ ID NO 40
<211> LENGTH: 51
<212> TYPE: DNA
<213> ORGANISM: Artificial Sequence
<220> FEATURE:
<223> OTHER INFORMATION: part of DNA of CCR5 gene
```

```
<400> SEQUENCE: 40
tttccataca gtcagtatca attctggaag aatttccaga cattaaagat a              51

<210> SEQ ID NO 41
<211> LENGTH: 19
<212> TYPE: DNA
<213> ORGANISM: Artificial Sequence
<220> FEATURE:
<223> OTHER INFORMATION: part of CCR5 delta 32

<400> SEQUENCE: 41
tttccataca ttaaagata                                                  19

<210> SEQ ID NO 42
<211> LENGTH: 1059
<212> TYPE: DNA
<213> ORGANISM: Artificial Sequence
<220> FEATURE:
<223> OTHER INFORMATION: CCR5 wild type sequence (NM_000579.4, No.358-
      1416)

<400> SEQUENCE: 42
atggattatc aagtgtcaag tccaatctat gacatcaatt attatacatc ggagccctgc     60
caaaaaatca atgtgaagca aatcgcagcc cgcctcctgc ctccgctcta ctcactggtg    120
ttcatctttg gttttgtggg caacatgctg gtcatcctca tcctgataaa ctgcaaaagg    180
ctgaagagca tgactgacat ctacctgctc aacctggcca tctctgacct gttttttcctt  240 cttactgtcc ccttctgggc tcactatgct gccgcccagt gggactttgg aaatacaatg    300
tgtcaactct tgacagggct ctattttata ggcttcttct ctggaatctt cttcatcatc    360
ctcctgacaa tcgataggta cctggctgtc gtccatgctg tgtttgcttt aaaagccagg    420
acggtcacct ttgggggtggt gacaagtgtg atcacttggg tggtggctgt gtttgcgtct   480
ctcccaggaa tcatctttac cagatctcaa aaagaaggtc ttcattacac ctgcagctct    540
cattttccat acagtcagta tcaattctgg aagaatttcc agacattaaa gatagtcatc    600
ttggggctgg tcctgccgct gcttgtcatg gtcatctgct actcgggaat cctaaaaact    660
ctgcttcggt gtcgaaatga aagaagagg cacagggctg tgaggcttat cttcaccatc    720
atgattgttt attttctctt ctgggctccc tacaacattg tccttctcct gaacaccttc    780
caggaattct ttgcctgaa taattgcagt agctctaaca ggttggacca agctatgcag    840
gtgacagaga ctcttgggat gacgcactgc tgcatcaacc ccatcatcta tgcctttgtc    900
ggggagaagt tcagaaacta cctcttagtc ttcttccaaa agcacattgc caaacgcttc    960
tgcaaatgct gttctatttt ccagcaagag gctcccgagc gagcaagctc agtttacacc   1020
cgatccactg gggagcagga aatatctgtg ggcttgtga                          1059
```